US006200565B1

(12) United States Patent
Weisbart

(10) Patent No.: US 6,200,565 B1
(45) Date of Patent: Mar. 13, 2001

(54) ORAL ADMINISTRATION OF IMMUNOGLOBULINS FOR TREATING AUTOIMMUNE HEARING LOSS

(75) Inventor: Richard H. Weisbart, Los Angeles, CA (US)

(73) Assignee: Research Corporation Technologies, Inc., Tucson, AZ (US)

( * ) Notice: Subject to any disclaimer, the term of this patent is extended or adjusted under 35 U.S.C. 154(b) by 0 days.

(21) Appl. No.: 09/306,772

(22) Filed: May 7, 1999

Related U.S. Application Data

(60) Provisional application No. 60/084,530, filed on May 7, 1998.

(51) Int. Cl.[7] .................................................. A61K 39/395
(52) U.S. Cl. ..................................... 424/130.1; 424/171.1
(58) Field of Search .............................. 424/130.1, 171.1

(56) References Cited

U.S. PATENT DOCUMENTS

| | | | |
|---|---|---|---|
| 5,422,282 | 6/1995 | Harris | 436/506 |
| 5,562,902 | 10/1996 | Shoenfeld et al. | 424/130.1 |
| 5,674,487 | 10/1997 | Smith et al. | 424/93.71 |
| 5,681,571 | 10/1997 | Holmgren et al. | 424/236.1 |

FOREIGN PATENT DOCUMENTS

| | | |
|---|---|---|
| WO 97 32598 | 9/1997 | (WO) . |
| WO 98 05777 | 2/1998 | (WO) . |

OTHER PUBLICATIONS

"New and controversial uses of intravenous gamma–globulin" (Pahwa, R. N.); *Pediatric Infectious Disease Journal*, 7(5) : S34–6, May 5, 1998, XP002112284 abstract.

Dwyer, J. M., (1996) "Immunoglobulins in autoimmunity: history and mechanisms of action", *Clinical and Experimental Rheumatology* 14 (Suppl.15): S3–S7.

Gardi, A., (1984) "Quality Control in the Production of an Immunoglobulin for Intravenous Use", *Blut*, 48:337–344.

Hicks et al., (1991) "Treatment of sensorineural hearing loss", *Indiana Medicine*, 84(8):540–544.

Kaveri et al., (1997) "Modulation of autoimmnue responses by intravenous immunoglobulin (IVIg)", *Multiple Sclerosis*, 3:121–128.

Leibl et al., (1996) "Method for the isolation of biologically active monomeric immunglobulin A from a plasma fraction", *Journal of Chromatography B: Biomedical Application*, 678:173–180.

Luetje, C., (1989) "Theoretical and Practical Implications for Plasmapheresis in Autoimmune Inner Ear Disease", *Laryngoscope*, 99:1137–1146.

Plester et al., (1989) "Autoimmune Hearing Loss", *The American Journal of Otology*, 10(3):188–192.

Sismanis et al., (1994) "Methotrexate Therapy for Autoimmune Hearing Loss: A Preliminary Report", *Laryngoscope*, 104:932–934.

Tjellström et al., (1997) "Oral immunoglobulin treatment in Crohn's disease", *Acta Paediatr*, 86:221–223.

*Primary Examiner*—Jean C. Witz
(74) *Attorney, Agent, or Firm*—Scully, Scott, Murphy & Presser

(57) ABSTRACT

The present invention is directed to methods of treating autoimmune sensorineural hearing loss in a patient by orally administering a human immunoglobulin preparation to the patient.

10 Claims, No Drawings

ORAL ADMINISTRATION OF IMMUNOGLOBULINS FOR TREATING AUTOIMMUNE HEARING LOSS

CROSS REFERENCE TO RELATED APPLICATION

This application claims priority from U.S. Provisional Application Ser. No. 60/084,530, filed on May 7, 1998.

FIELD OF THE INVENTION

This invention relates generally to the treatment of hearing loss, and particularly to the treatment of autoimmune sensorineural hearing loss by oral administration of a preparation of human immunoglobulins.

BACKGROUND OF THE INVENTION

Of the 25 million people who are hearing impaired, 85% suffer from sensorineural hearing loss (SNHL), a loss of hearing due to decreased hearing nerve function. There are various forms of inner ear disorders causing SNHL, including Meniere's disease, viral labyrinthitis, perilymph fistula, otosyphilis, and congenial or hereditary deafness. Sensorineural hearing loss is generally accompanied by ear fullness, tinnitus and disturbance of balance. A number of medical, dietary and surgical treatments are available for SNHL. See, e.g., Hicks and Wright III (1991) *Indiana Medicine* 84(8): 450–544.

Autoimmune sensorineural hearing loss (ASNHL) has been considered by some as a separate entity of SNHL and by others as a cause for various forms of SNHL. ASNHL is characterized by progressive unilateral or bilateral deafness that, in its incipient stages, may fluctuate or become sudden and profound. The symptoms of ASNHL are quite similar to other forms of SNHL. ASNHL is believed to occur when the body's immune system attacks and progressively destroys the inner ear. The pathogenesis of ASNHL includes vasculitis of vessels supplying the inner ear, autoantibodies directed against inner ear antigenic epitopes or cross-reacting antibodies. See, e.g., Hicks and Wright III (1991) and U.S. Pat. No. 5,422,282 to Harris.

A traditional line of therapy for ASNHL has been oral or parenteral administration of various immunosuppressants including steroids, cytotoxic drugs (such as cyclophosphamide) or methotrexate. Steroid therapy is associated with various side effects, such as weight gain, facial puffiness and constitutional changes (Sismanis et al., *Laryngoscope* 104: 932–934, 1994). Cyclophosphamide has dramatic adverse effects as well, e.g., severe nausea and vomiting, thrombocytopenia, leukopenia and hemorrhagic cystitis (Sismanis et al., 1994). Methotrexate appears to be less toxic. However, large scale studies are required to confirm the efficacy of methotrexate for treating ASNHL (Sismanis et al., 1994). Plasmapheresis has been suggested as an alternative therapy for patients who are intolerant to steroids and/or cyclophosphamide, but has been considered as impractical (Luetje *Laryngoscope* 99: 1137–1146, 1989).

Despite the different therapies currently available, there is a need for more effective methods of treating ASNHL with fewer accompanying side effects. The present invention provides effective methods for treating ASNHL by oral administration of a human immunoglobulin preparation.

SUMMARY OF THE INVENTION

The present invention provides a method of treating autoimmune sensorineural hearing loss in a patient in need thereof which comprises orally administering to the patient an effective amount of a human immunoglobulin preparation. Human immunoglobulin preparations suitable for use in the methods of the present invention can be made by any of the well-known methods used for preparing parenteral immunoglobulin preparations. Suitable IG preparations can also be obtained commercially. The human immunoglobulin preparation may include any of the known IG classes including IgA, IgG, IgM, IgE, and IgD. Preferably, the human immunoglobulin preparation comprises at least one of immunoglobulin G (IgG) or immunoglobulin A (IgA). Preparations of fragments of human immunoglobulins can also be used in accordance with the present invention. The immunoglobulin preparation is preferably provided in a pharmaceutically acceptable carrier and orally administered at about 0.2 to about 5 grams per day. Preferably, the immunoglobulin preparation is administered in two to five separate doses at about 0.15 grams to about 1 grams per dose.

In accordance with the present invention, oral administration of a human IG preparation may be accomplished alone or in combination with other treatment regimes.

DETAILED DESCRIPTION OF THE INVENTION

The present invention relates to methods of treating a subject suffering autoimmune sensorineural hearing loss (ASNHL) by oral administration of a human immunoglobulin (IG) preparation.

The term "subject" as used herein, is taken to mean any mammalian patient to which an IG preparation is orally administered according to the methods described herein. In a preferred embodiment, the methods of the present invention are employed to treat a human subject.

ASNHL is a form of sensorineural hearing loss caused by a malfunction of the body's immune system which attacks and progressively destroys the inner ear. ASNHL can be diagnosed by a combination of standard physical exams and laboratory tests. Physical exams can include microscopic ear examination, neurological examination, audiologic evaluation by measuring air and bone conduction with speech discrimination, and electrocochleography. Patients with a bilateral or asymmetric sensorineural deafness for which the cause is not readily apparent are suspect for ASNHL. Such patients can be further examined by laboratory tests, e.g., serological assays for complete blood count with differential and Sequential Multiple Analysis of 20 chemical constituents (SMA-20), erythrocyte sedimentation rate, fluorescent treponemal antibody absorption (FTA-Abs) test, antinuclear antibody titer, rheumatoid factor, quantitation of IgA and IgG. See, e.g., Hicks and Wright III (1991) and Sismanis et al. (1994). Laboratory tests can also include those which are based on the determination of non-specific or specific autoantibodies in the patient's serum or inner ear fluid. See, e.g., Plester and Soliman, *The American Journal of Otology* 10(3): 188–192, 1989 and U.S. Pat. No. 5,422,282.

According to the present invention, a subject suspected of having ASNHL can be treated by orally administering a therapeutically effective amount of a human immunoglobulin preparation.

As used herein, "treating" and "treatment" refer to administering to a subject a therapeutically effective amount of a human IG preparation so that the impairment in the ear substructures caused by autoimmune disorder is suppressed, inhibited and/or ameliorated thereby stabilizing or improving the auditory function of the subject. The therapeutic effects of an IG preparation are believed to result from a blockade of Fc-Receptors, a neutralization of an autoantibody by anti-idiotype antibodies present in the IG preparation, binding and down-regulation by anti-idiotype antibodies of the B-cell receptor for an antigen thereby decreasing the autoantibody production, or combinations thereof. See Dwyer (1996) in *Clinical and Experimental Rheumatology* 14 (suppl. 15): S3–S7.

According to the present invention, it is indicated that orally administered human immunoglobulins can be absorbed and processed by specialized cells in the mucosa tissues of the digestive tract, e.g., epithelial enterocytes and Peyer's patch M cells in the gut-associated lymphoid tissue, which permits the establishment of self-tolerance and inhibition of autoimmunne reactions in the ASNHL patients.

According to the present invention, an immunoglobulin preparation suitable for practicing the present invention may contain varying amounts of IgA, IgG, IgM, IgE, or IgD. In a preferred embodiment of the present invention, the IG preparation is made up of predominantly IgG or IgA immunoglobulins. The compositions useful for practicing the methods of the present invention may also contain other immunoglobulins such as IgM, IgD or IgE.

In accordance with the present invention, fragments of immunoglobulins are also suitable for practicing the methods of the present invention. As used herein, "fragments of immunoglobulins" refer to portions of intact immunoglobulins such as Fc, Fab, Fab', $F(ab')_2$ and single chain immunoglobulins.

The human immunoglobulins to be orally administered in accordance with the present invention can be prepared from human blood by employing the procedures that are used in preparing immunoglobulins for parenteral administration, e.g., immunoglobulins prepared for intravenous administration (also called IVIG). Normally, blood is collected and pooled from a number of healthy volunteers. According to the present invention, the number of blood donors is at least about 5 or 10; preferably, at least about 100; more preferably, at least about 1000; yet more preferably, at least about 10,000.

Immunoglobulins can be isolated from the pooled human blood by a number of well-known methods. Such methods include Cohn's alcohol fractionation (Cohn et al., *J. Am. Chem. Soc.* 68:459–475,1946; Oncley et al., *J. Am. Chem. Soc.*, 71: 541–550, 1949), fractionation (Schneider et al., *Vox Sang.*31: 141–151, 1976), ultracentrifugation (Barundern et al., *Vox Sang.* 7: 157–174, 1962), or the method of Kistler and Nitschmann (*Vox Sang* 7: 414–424, 1962), polyelectrolyte affinity adsorption, large scale electrophoresis, ion exchange adsorption, and polyethylene glycol fractionation. Any method which fractionates immunoglobulins from a human source may be used to obtain immunoglobulins suitable for use in practicing the methods of the present invention.

Immunoglobulins fractionated from pooled human blood contain predominantly IgG, smaller amounts of IgA, and yet smaller or trace amounts of IgM, IgE, IgD, with a diverse spectrum of antibody specificities and subclass distribution charateristic of the donor population. Such a preparation may also contain cytokines from the plasma, e.g., TGF-β. Additional preparative steps can be used to enrich a particular class of immunoglobulin. For example, protein G sepharaose treatment can lead to an IgA predominant preparation as described by, e.g., Leibl et al. *J. Chromatogr B. Biomed. Appl.* 678(2): 173–180 (1996). In addition, conventional methods can be employed for producing fragments of immunoglobulins. Such methods are taught by, e.g., Coligan et al., *Current Protocols in Immunology*, John Wiley & Sons Inc., New York, N.Y. (1994).

According to the present invention, further preparative steps can be used in order to render an immunoglobulin preparation safe for use in the methods of the present invention. Such steps can be the same as those for rendering IVIG safe, which include, but are not limited to, enzymatic modification (Fahey et al., *J. Exper. Med.*,118: 845–868, 1963; Kneapler et al., *Vox Sang.*32: 159–164, 1977), chemical modification (Stephan, *Vox Sang.* 28: 422–437, 1975; Masuko et al., *Vox Sang.* 32: 175–181, 1977), reduction and alkylation (U.S. Pat. No. 3,903,262 to Pappenhagen et al.), sulfonation, structural modification (Barundern et al., *Mong. Allergy* 9: 39–60, 1975), treatment with β-propiolactone, treatment at low pH (Barandun et al., *Vox Sang.* 7: 157–174, 1962; Koblet et al., *Vox Sang.*31: 141–151, 1976), purification by ion exchange chromatography, treatment with solvent/detergent, pasteurization and sterilization. Descriptions of these methods can also be found in, e.g. Romer et al., *Vox Sang.* 42: 62–73, 1982; Romer et al., *Vox Sang.* 42: 74–80, 1990; and Rutter, *J. Neurosurg. Psychiat.* 57 (Suppl.): 2–5, 1994. β-propiolactone in particular, has proven very effective in eliminating a number of enveloped and nonenveloped viruses including hepatitis C and human immunodeficiency virus (HIV) (Dichtelmuller, *Biologicals* 21: 259–268, 1993; Stephan, *J. Med. Virol.* 26: 227–232, 1975).

In accordance with the present invention, the safety standards of an IG preparation for oral administration can be the same as those proposed for IVIG. For example, standards for the preparation of IVIG were proposed in 1989 in a World Health Organization (WHO) bulletin and updated in 1989 to increase the safety of prepared immunoglobulins and other blood products. Safety tests which can be performed may include, e.g., sterility test, Pyrogen test, Hepatitis B antigen test, anticomplementary activity test and the like. See, e.g., A. Gardi (1984) Blut 48: 337–344.

In accordance with the present invention, immunoglobulins isolated from pooled human blood are preferably made into powders by conventional freeze-drying (or lyophilization) procedure. Preferably, one or more stabilizing substances are added to the immunoglobulin preparation prior to the freeze-drying process. A variety of stabilizing substances can be employed including, e.g., amino acids such as glycine and lysine, carbohydrates such as dextrose, mannose, galactose, fructose, lactose, sucrose, maltose, sorbitol, mannitol and the like.

An immunoglobulin preparation in lyophilized form for use in practicing the methods of the present invention can also be obtained through commercial sources. Such sources include but are not limited to: Gammagard S/D® (Baxter Healthcare), Sandoglobulin I.V.® (Sandoz Pharmaceuticals), Polygam S/D® (American Red Cross), Venoglobulin®-I (Alpha Therapeutic), VZIG® (American Red Cross), IgAbulin® (Immuno AG, Vienna, Austria) and Intraglobin-F® (Biotest Pharma GmbH, Frankfurt, Germany). The efficacies of IVIG preparations from different commercial sources have been shown to be comparable in various therapeutic applications. See, e.g., Schiff, R. I., et al. 1977 *J. Clin. Immun.* 17(1):21–28; Haque, K. N., et al., 1995 *Clin. Exp. Immunol.* 101:328–333; and U.S. Pat. No. 5,562,902 to Shoenfeld et al.

A preferred commercial source of IG appropriate for use in the methods of the present invention is Sandoglobulin I.V.® (Sandoz Pharmaceuticals), which contains 96% IgG with traces of IgA and IgM.

Another preferred commercial source of IG is IgAbulin® (Immuno AG, Vienna, Austria), which contains predominantly IgA.

Further in accordance with the present invention, the human IG preparation suitable for oral administration is preferably provided in a pharmaceutically acceptable carrier with or without an inert diluent. The carrier should be assimilable and edible and includes liquid, semi-solid, e.g. pastes, or solid carriers. Except insofar as any conventional media, agent, diluent or carrier is detrimental to the recipient or to the therapeutic effectiveness of an IG preparation contained therein, its use in an orally administrable immunoglobulin for use in practicing the methods of the present invention is appropriate. Examples of carriers or diluents include fats, oils, water, saline solutions, lipids, liposomes, resins, binders, fillers and the like, or combinations thereof.

In accordance with the present invention, the IG can be combined with the carrier in any convenient and practical manner, e.g., by solution, suspension, emulsification, admixture, encapsulation, absorption and the like. Such procedures are routine for those skilled in the art.

In a preferred embodiment of the present invention, a human IG preparation in powder form is combined or mixed thoroughly with a semi-solid or solid carrier. The mixing can be carried out in any convenient manner such as grinding. Stabilizing agents can be also added in the mixing process in order to protect the IG from loss of therapeutic activity through, e.g., denaturation in the stomach. Examples of stabilizers for use in an orally administrable immunoglobulin preparation include buffers, antagonists to the secretion of stomach acids, amino acids such as glycine and lysine, carbohydrates such as dextrose, mannose, galactose, fructose, lactose, sucrose, maltose, sorbitol, mannitol, etc., proteolytic enzyme inhibitors, and the like.

Futher in accordance with the present invention, an IG preparation which is combined with a semi-solid or solid carrier can be further formulated into hard or soft shell gelatin capsules, tablets, or pills. More preferably, such gelatin capsules, tablets, or pills are enterically coated. Enteric coatings can prevent denaturation of IG in the stomach or upper bowel where the pH is acidic. See, e.g., U.S. Pat. No. 5,629,001 to Michael et al. Upon reaching the small intestines, the basic pH therein dissolves the coating and permits IG to be released and absorbed by specialized cells, e.g., epithelial enterocytes and Peyer's patch M cells.

In another preferred embodiment, a powdered human IG preparation is combined with a liquid carrier such as, e.g., water or a saline solution, with or without a stabilizing agent. Such IG preparations reconstituted in solutions can also be obtained through commercial sources. Such commercial sources include BayRho-D® Full Dose (Bayer Biological), BahRho-D® Mini-Dose (Bayer Biological), Gamimune N®, 5% (Bayer Biological), Gamimune N®, 5% Solvent/Detergent Treated (Bayer Biological), Gamimune NO, 10% (Bayer Biological), Gamimmune N 5% (Miles), Gammagard S/D® (Baxter Healthcare), Isiven V.I. 2.5% (Isiven), MICRhoGAM® (Ortho Diagnostic), RhoGAM® (Ortho Diagnostic), Sandoglobulin I.V.® (Sandoz Pharmaceuticals), Polygam S/D® (American Red Cross), Venoglobulin-S® 5% Solution Solvent Detergent Treated (Alpha Therapeutic), Venoglobulin-S® 10% Solution Solvent Detergent Treated (Alpha Therapeutic), and IgAbulin® (Immuno AG, Vienna, Austria).

In accordance with the present invention, an IG preparation provided in any of the above-described pharmaceutical carriers can be orally administered to a subject suspected of having ASHL. The precise therapeutically effective amount of IG preparation to be administered can be determined by a physician with consideration of individual differences in age, weight, disease severity and response to the therapy. It can generally be stated that in practicing the methods of the present invention, an IG preparation should be administered to a patient suspected of having autoimmune-related hearing loss at about 0.2 grams to about 5 grams each day. In a preferred embodiment, an IG preparation is administered about two to five times a day at a dose of about 0.15 grams to about 1 gram each time. In a more preferred embodiment, a dose range of about 0.25 grams is administered four times a day. The IG preparation can be administered before, during, or after a meal. Preferably, the IG preparation is administered before a meal.

To further reduce the degree of inactivation of an IG in the stomach of an individual undergoing treatment according to the methods of the present invention, an antacid may be administered just prior or immediately after oral administration of the IG. An antacid may also be given simultaneously with the IG. Examples of appropriate antacids include sodium bicarbonate, magnesium oxide, magnesium hydroxide, calcium carbonate, magnesium trisilicate, magnesium carbonate, and aluminum hydroxide gel. Preferably, the antacid is aluminum hydroxide or magnesium hydroxide such as Maalox® or Mylanta®, which are commercially available. Most preferably, the antacid is an H2 blocker such as Cimetidine or Ranitidine. Preferable dose ranges are between 15 ml and 30 ml for Mylanta, and between 400 and 800 mg per day for cimetidine.

In accordance with the present invention, the time needed to complete a course of the treatment can be determined by a physician and may range from as short as one day to more than one week. A preferred course of treatment is from 2 to 6 weeks. In a more preferred embodiment, a course of treatment lasts for six weeks. A course of treatment may be repeated as often as necessary, as determined by a physician, in order to maintain or extend the therapeutic benefit to the patient.

The methods of the present invention may be performed on patients suffering autoimmune hearing loss in conjunction with conventional treatments. Thus, such patients can undergo the methods of the present invention during the course of other treatment procedures, i.e., administration of steroid, cyclophosphamide, methotrexate and other drugs. The methods of the present invention may also be administered during the course of enteral nutrition treatments, i.e., either before, after, or simultaneously with such treatments.

In another aspect of the invention, oral administration of immunoglobulins according to the methods of the present invention may be provided to patients suffering autoimmune hearing loss after other, conventional procedures such as drug therapy and/or surgery have been suspended or completed.

Patients treated according to the methods of the present invention may exhibit stabilized or improved hearing, reflected by, e.g., improved speech and/or tone discrimination, subsided symptoms of ear fullness, tinnitus or vertigo. Patients treated according to the methods of the present invention may have an improved condition according to other indicators as well, such as disappearance of autoantibodies in the serum or inner ear fluid, restored normal serum content of IgG and IgA, or the like.

All the publications mentioned in the present disclosure are incorporated herein in their entirety by reference. The terms and expressions which have been employed in the present disclosure are used as terms of description and not of limitation, and there is no intention in the use of such terms and expressions of excluding any equivalents of the features shown and described or portions thereof, it being recognized that various modifications are possible within the scope of the invention.

What is claimed is:

1. A method of treating autoimmune sensorineural hearing loss in a patient in need thereof which comprises orally administering to the patient an effective amount of a human immunoglobulin preparation.

2. The method according to claim 1 wherein the immunoglobulin is at least one of immunoglobulin G (IgG) or immunoglobulin A (IgA).

3. The method according to claim 1 wherein the immunoglobulin preparation is provided in a pharmaceutically acceptable carrier.

4. The method according to claim 3 wherein said pharmaceutically acceptable carrier is a liquid, semi-solid or solid.

5. The method according to claim 4 wherein said pharmaceutically acceptable carrier is semi-solid or solid.

6. The method according to claims 5 wherein said pharmaceutically acceptable carrier is enterically coated.

7. The method according to claim 4 wherein said pharmaceutically acceptable carrier is liquid.

8. The method according to claim 3 wherein said human immunoglobulin preparation is Sandoglobulin I.V.® (Sandoz Pharmaceuticals).

9. The method according to claim 1 wherein the amount of immunoglobulin administered to said patient is from about 0.2 to about 5 grams at least once a day.

10. The method according to claim 1 wherein the immunoglobulin preparation is administered with an antacid or H2 blocker.

* * * * *